United States Patent [19]
Sapiejewski

[11] Patent Number: 5,305,387
[45] Date of Patent: Apr. 19, 1994

[54] EARPONING

[75] Inventor: Roman Sapiejewski, Boston, Mass.

[73] Assignee: Bose Corporation, Framingham, Mass.

[21] Appl. No.: 427,767

[22] Filed: Oct. 27, 1989

[51] Int. Cl.⁵ .................... G10K 11/16; A61F 11/02
[52] U.S. Cl. ................................ 381/71; 381/72; 381/94
[58] Field of Search .................. 381/71, 72, 94, 74

[56] References Cited

U.S. PATENT DOCUMENTS

| | | |
|---|---|---|
| 3,890,474 | 6/1975 | Glicksberg ........................ 381/82 |
| 4,870,688 | 9/1989 | Voroba et al. ................... 38/68.6 |
| 4,985,925 | 1/1991 | Langberg et al. ................ 381/72 |

FOREIGN PATENT DOCUMENTS 2604551  4/1988  France.

Primary Examiner—Forester W. Isen
Attorney, Agent, or Firm—Fish & Richardson

[57] ABSTRACT

An earphone for use in an active noise reduction system includes a shell accommodating a microphone closely adjacent to a driver shaped and sized to fit in the concha of an ear.

22 Claims, 6 Drawing Sheets

EARPONING

The present invention relates in general to earphoning and more particularly concerns novel apparatus and techniques for actively reducing noise in earphones of especially lightweight compact structure.

For background reference is made to U.S. Pat. Nos. 4,644,581 and 4,455,675 and copending U.S. application Ser. No. 07/138,095, incorporated herein by reference. According to those inventions, there is a headphone cavity and electroacoustical transducer, such as a pressure sensitive microphone, within the cavity for providing a signal corresponding to the sum of external noise and the sound produced by a headphone driver, in the same cavity. A combiner combines this transduced signal with the input signal desired to be reproduced to produce an error signal representative of the noise and other differences between the input signal to be reproduced and the output of the headphone driver in the cavity. A servo comprising the combiner includes a compensator that compensates for these error signals to produce an output acoustical signal at the ear with external noise and distortion significantly reduced and with substantially uniform frequency response between the input to which the signal desired to be reproduced is applied and the ear.

It is an important object of this invention to provide an improved earphone in an active noise reducing system that is lightweight, compact and comfortable.

According to the invention, there is an assembly including a first electroacoustical transducer for transducing electroacoustical energy into an electrical signal and a second electroacoustical transducer closely adjacent to the first electroacoustical transducer for transducing electrical energy into acoustical energy in a shell small enough to be placed inside the concha of the ear. According to one aspect of the invention the shell is formed to fit inside a number of ear conchae. According to another aspect of the invention, the shell is custom molded to fit inside the concha of an individual user. According to another aspect of the invention, the second electroacoustical transducer at least in part is on the boundary between an inside or front cavity closer to the inner ear than an outside or rear cavity further from the inner ear. The first electroacoustical transducer is located inside the front cavity close to the second electroacoustical transducer. The first electroacoustical transducer is typically a microphone having a microphone diaphragm perpendicular to the driver diaphragm of the second electroacoustical transducer, typically an earphone driver preferably heavily damped. According to another aspect of the invention the shell is formed with an inside opening facing the second electroacoustic transducer and covered by acoustically resistive material, such as fine wire mesh. According to another aspect of the invention, the rear cavity is a tube coaxially surrounded at least in part by a portion of the front or inside cavity with each of the cavities preferably largely filled with open cell foam. Preferably a layer of polyurethane film encloses a layer of silicone gel along a portion of the outside of the shell.

Numerous other features and advantages of the invention will become apparent from the following detailed description when read in connection with the accompanying drawing in which:

FIG. ; is a block diagram illustrating a system embodying the invention;

Figure 1:
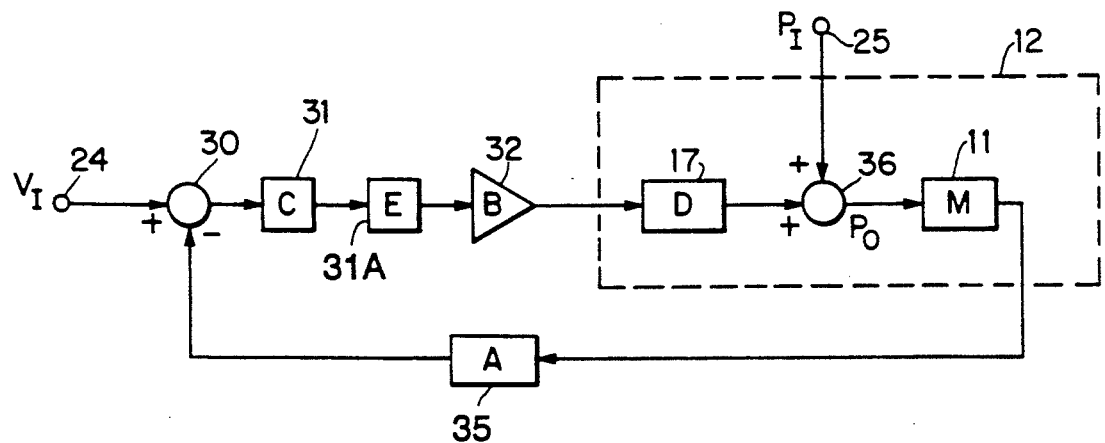

With reference now to the drawing and more particularly FIG. 1 thereof, there is shown a block diagram illustrating the logical arrangement of a system incorporating the invention corresponding substantially to FIG. 1 of the aforesaid '581 patent. A signal combiner 30 algebraically combines the signal desired to be reproduced by the earphone on input terminal 24 with a feedback signal provided by microphone preamplifier 35. Signal combiner 30 provides the combined signal to compressor 31 which limits the level of the high level signals. The output of compressor 31 is applied to compensator 31A. Compensator 31A includes compensation circuits to insure that the open loop gain meets the Nyquist stability criteria, so that the system will not oscillate when the loop is closed. The system shown is duplicated once each for the left and right ears.

Power amplifier 31 amplifies the signal from compensator 31A and energizes earphone driver 17 to provide an acoustical signal in cavity 12 that is combined with an outside noise signal that enters cavity 12 from a region represented as acoustical input terminal 25 to produce a combined acoustic pressure signal in cavity 12 represented as a circle 36 to provide a combined acoustic pressure signal applied to and transduced by microphone 11. Microphone amplifier 35 amplifies the transduced signal and delivers it to signal combiner 30.

Figure 2:
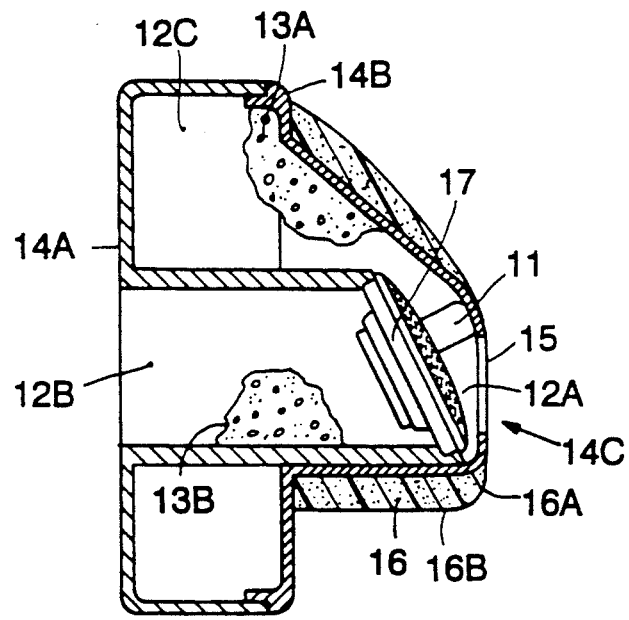
FIG. 2 is an axial sectional view of an embodiment of the invention.
Figure 2A:
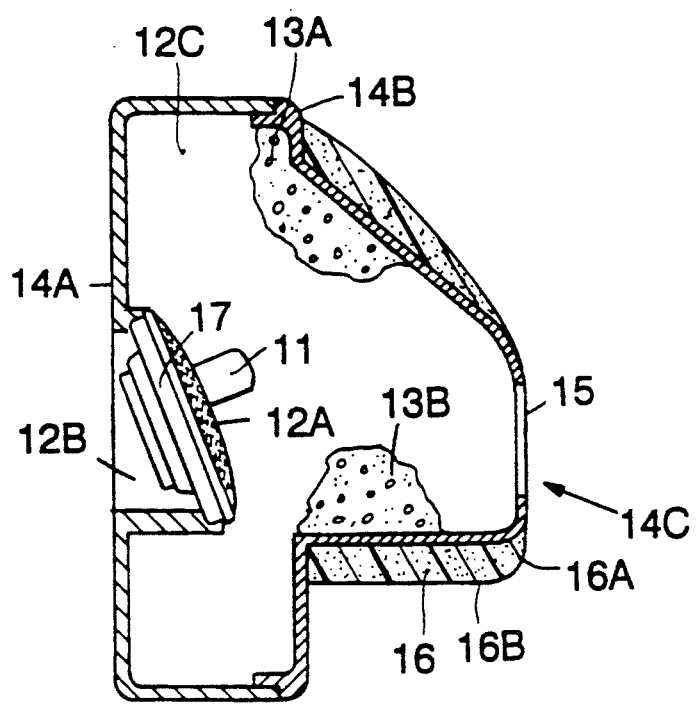
FIG. 2A shows an embodiment of the invention in which the front cavity occupies most of the volume of the shell.

Referring to FIG. 2, there is shown a diametrical sectional view of an embodiment of the invention. Microphone 11 is shown positioned in front cavity 12A with driver 17, preferably heavily damped, located along the boundary between inner or front cavity 12A and outer or rear cavity 12B. Front or inner cavity 12A has a portion 12C coaxially surrounding rear or outer cavity 12B. Rear or outer cavity 12B and front cavity 12A including portions 12C are filled with open cell foam 13B and 13A, respectively. A shell 14 typically made of plastic includes a rear or outer portion 14A and front or inner portion 14B joined together with front or inner portion 14B formed with an opening 14C covered by acoustic resistive material 15, such as fine wire mesh. A cushion 16 is made of silicon gel 16A covered by polyurethane film 16B and is shaped to provide comfort and seal to different ears without moving microphone 11 away from the entrance to the ear canal. The rear or outer side of the diaphragm of driver 17 is exposed to the outside through rear or outer cavity 12B open at the outside as shown.

Having described structural arrangements certain principles of the invention will be described. The invention is relatively compact and lightweight while providing comfort to the wearer. Locating structure in the concha of the ear allows reduction of size and weight as compared with structures having large earcups and large circumaural cushions. The invention still provides significant noise attenuation.

An important aspect of the system is maintaining stability. The invention includes structure modifying the transfer function between driver 17 and microphone 11 so as to provide sufficient gain and phase margins. The transfer function depends not only on the transducers, but also the acoustics of the cavity in which the transducers are located and differs from one user to another having different concha characteristics. At high frequencies variations are caused by variation in human ear canals, volumes, sizes and eardrum impedances. The effect of these variations on the transfer function may be reduced by establishing a relatively large volume in the front or inner cavity 12A.

Figure 3:
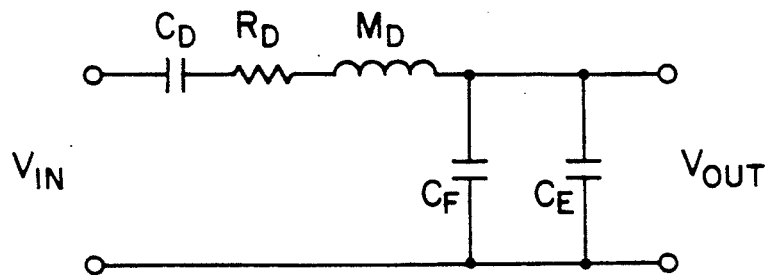
FIGS. 3 and 4 are equivalent electrical circuits characterizing the transfer function of a system according to the invention at high and low frequencies, respectively.
Figure 4:
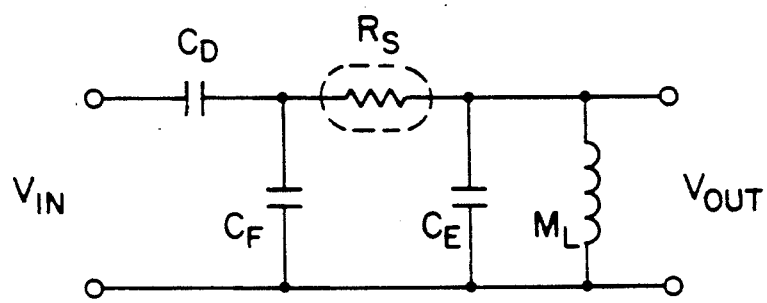

Referring to FIGS. 3 and 4, there are shown a simplified equivalent electrical circuits characterizing the transfer function of the system at high and low frequencies, respectively. $C_D$ is driver 17 compliance, $M_D$ is driver 17 mass, $C_F$ is compliance of front or inner cavity 12A, $C_E$ is compliance of the ear canal cavity, and $R_D$ is driver 17 resistance. If the front cavity volume is chosen to satisfy the condition $C_D > C_F > C_E$, then the transfer function can be approximated by:

$$\frac{v_o}{V_{IN}} \approx \frac{1}{S^2 M_D C_F + 1}$$

and is not a function of the ear canal compliance. (The average volume of an ear canal is about 2 cc.

In FIG. 4 $R_s$ is the resistance of acoustic resistance 15 and $M_L$ represents mass of the leak between front cavity 12A and the concha. Without resistive screen 15, response of the system has a second order roll-off which causes 180° phase shift that would cause a stability problem. The problem could be overcome by electronic compensation at low frequencies; however, this approach would limit the dynamic range of the system. A preferred approach according to the invention is to place resistive element 15 in the opening 14C of shell 14B at the front or inner cavity 12A. The resistive element is preferably chosen with resistance low enough to so that it won't significantly effect cancellation.

Figure 5A:
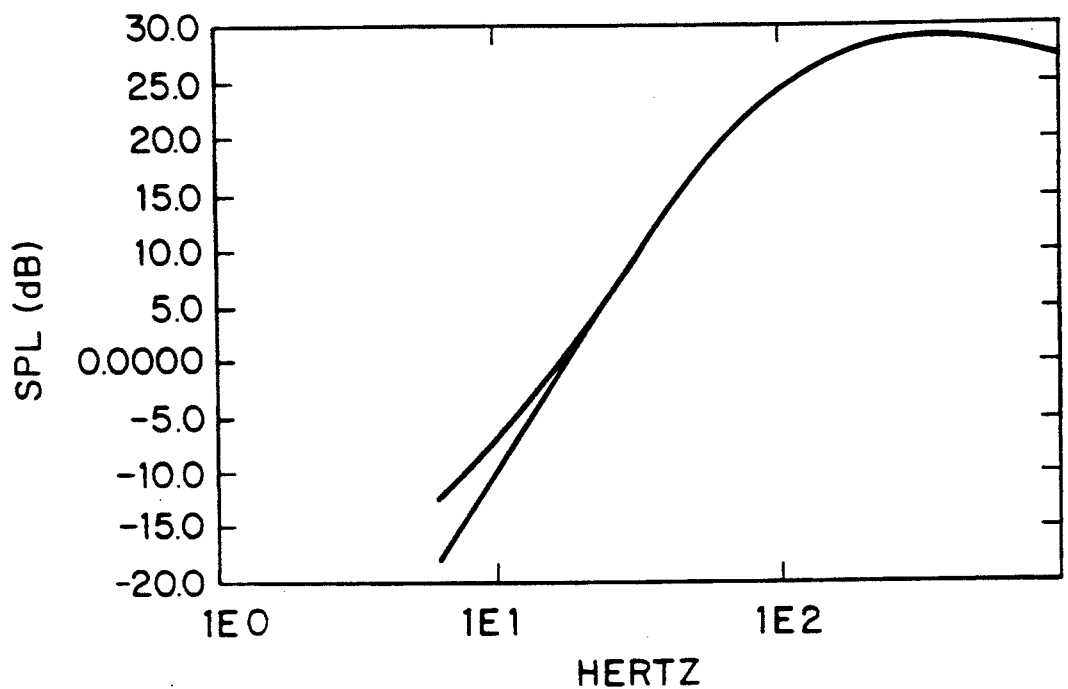
FIGS. 5A and 5B are graphical representations of the effect of the resistive screen on magnitude and phase responses, respectively, of the system.
Figure 5B:
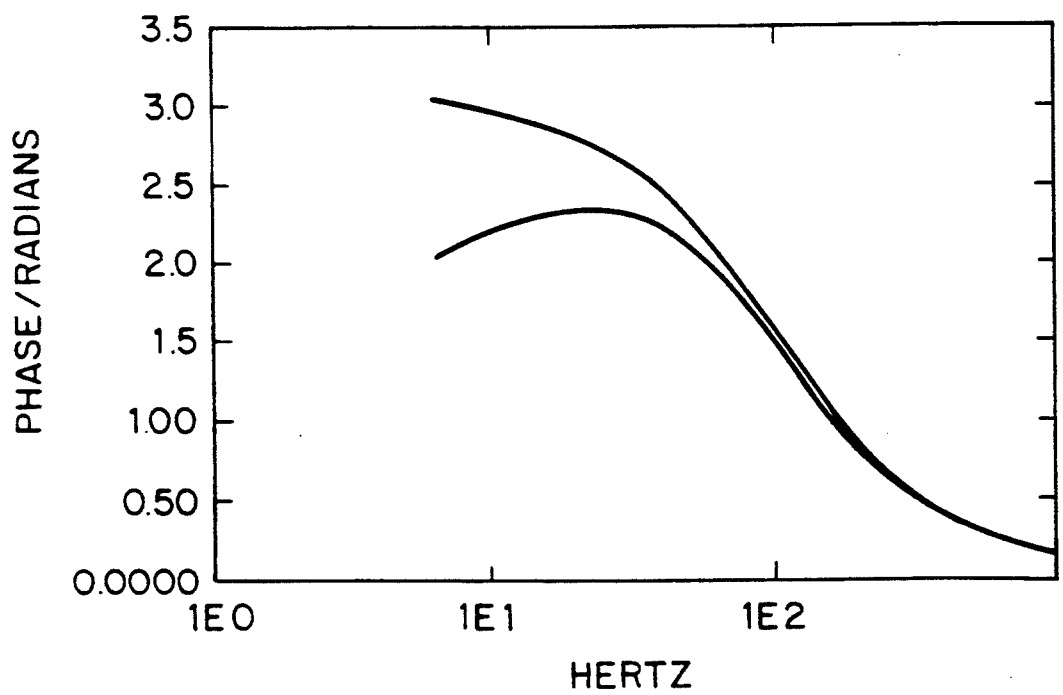

Referring to FIGS. 5A and 5B, there are shown graphical representations of the effect of resistive screen 15 on amplitude and phase response, respectively, of the system showing the relatively slight attenuation introduced by the resistive screen with system responses being represented by the lower curves and the avoidance of the 180° phase shift.

An advantage of the invention is that by using a smaller driver 17 and by placing the sensing microphone 11 close to the entrance of the ear canal, the bandwidth of the active cancellation may be extended up to 1500 Hz, of the order of twice as high as practically available with a circumaural system disclosed in the aforesaid patents. Another feature of the invention is that it is characterized by a significant amount of passive attenuation at high frequencies to provide effective noise protection. Passive attenuation is a function of the leak and volume of the front or inner cavity. It was discovered that for a small structure, this volume preferably should not exceed more than about 10 cc. It was found that the preferred approach to passive attenuation is to use almost the entire available volume of the shell as a front cavity with none or negligible back cavity volume.

Figure 6:
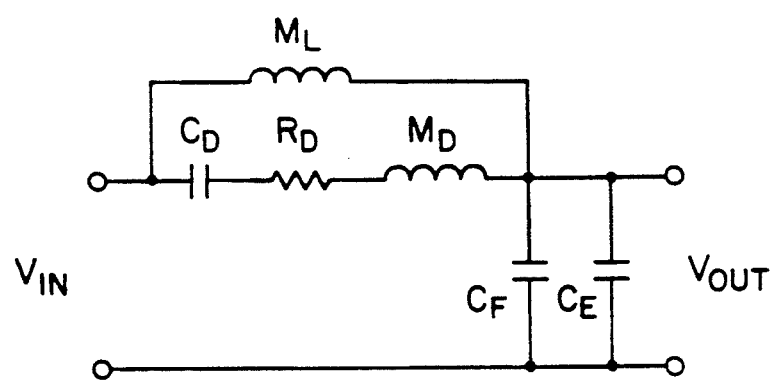
FIG. 6 is an equivalent electrical circuit modeling passive transmission loss of the system.

Referring to FIG. 6, there is shown an equivalent electrical circuit for passive transmission loss analysis. It was determined experimentally that even with a very good seal, the leak mass $M_L$ dominates over driver impedance $C_D$, $R_D$, $M_D$, and the open back of the driver through rear cavity 12B does not deteriorate the system performance significantly.

Figure 7:
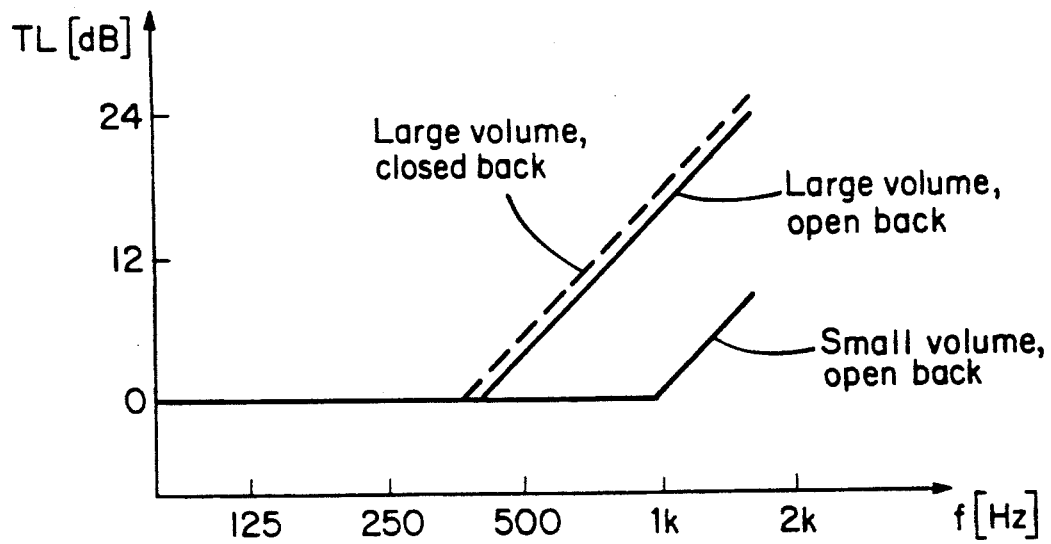
FIG. 7 illustrates the effect of volume at the front or inner cavity and open back on the passive attenuation.

Referring to FIG. 7, there is shown a graphical representation illustrating the negligible difference in passive attenuation when the front or inner cavity is large with closed or open back providing significantly better passive attenuation than using a small volume front or inner cavity with an open back.

Figure 8:
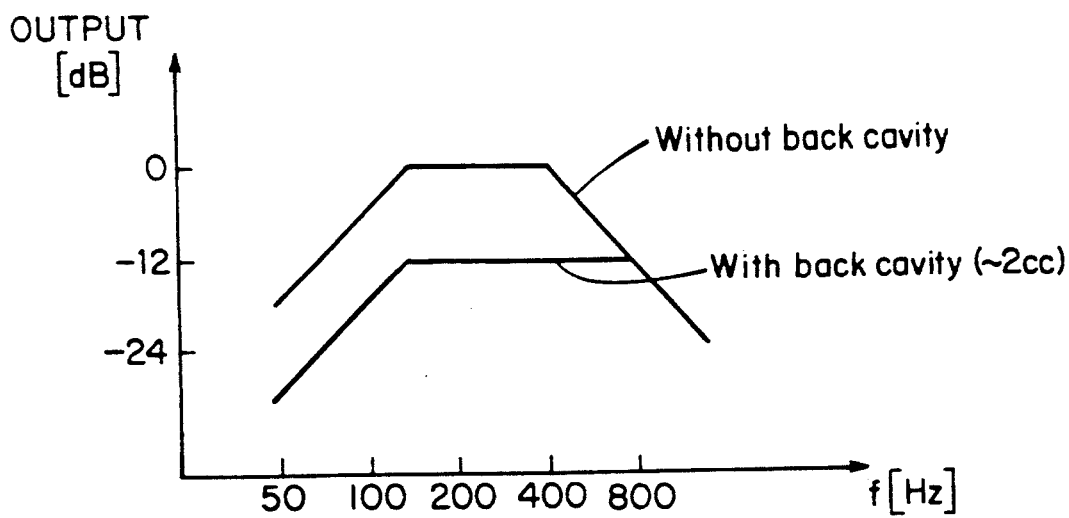
FIG. 8 illustrates the effect of the back cavity of two cc on driver efficiency.

A feature of the invention is the use of a very small driver 17 resulting in broader cancellation bandwidth in a small structure. Driver maximum power handling capability is typically related to the driver size, and the driver efficiency is typically related to the volume of the rear or outer cavity 12B. For higher output it is desirable to use no back or outer cavity at all. Referring to FIG. 8, there is shown a graphical representation showing the increased output without back cavity compared with the output with a rear or outer cavity of the order of 2 cc.

Figure 9:
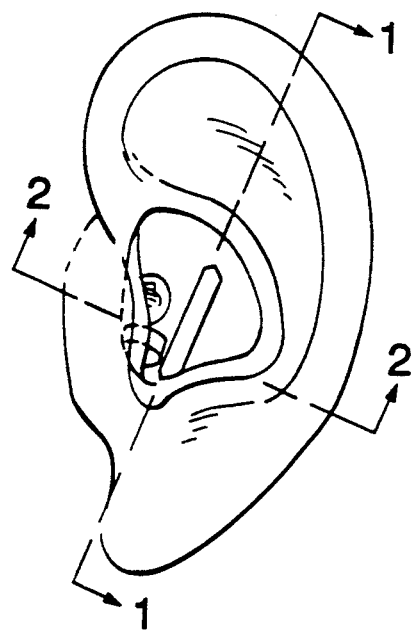
FIG. 9 is a plan View showing elements of an embodiment of the invention in the left ear.
Figure 9A:
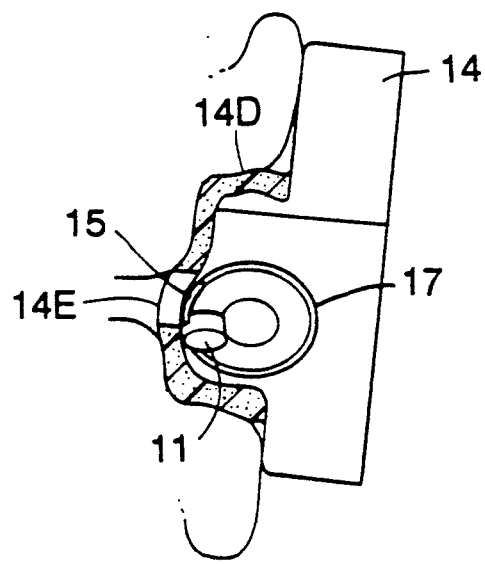
FIG. 9A is a view through section 1—1 of FIG. 9.
Figure 9B:
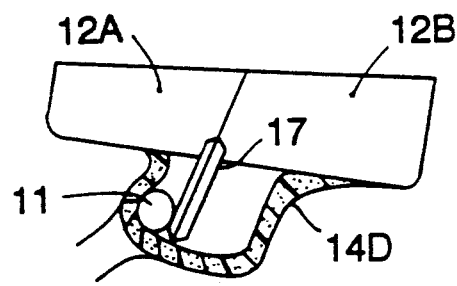
FIG. 9B is a view through section 2—2 of FIG. 9.

A preferred form of the invention comprises a shell structure having a custom fit piece for each ear. Referring to FIG. 9, there is shown a plan view of a form of the invention. FIGS. 9A and 9B show sectional views through section 1—1 and 2—2, respectively of FIG. 9 illustrating the custom snap-on ear cavity mold 14D that snaps on shell 14 formed with an opening 14E at the entrance to the ear canal exposing acoustic resistance 15. Driver 17 and microphone 11 are oriented as shown with the diaphragm of driver 17 perpendicular to the concha axis. Custom ear cavity mold 14D may be fabricated in substantially the same manner as custom molds for hearing aids.

There has been described novel apparatus and techniques for providing compact lightweight earphones in a system that provides significant active noise cancellation. Other embodiments are within the claims.

What is claimed is:

1. Earphone apparatus in an active noise reduction system comprising:

an assembly including a shell accommodating first and second closely adjacent electroacoustical transducers of shape and size that allows said shell and first and second electroacoustical transducers to fit inside the concha of the ear, said shell being formed with at least a front cavity characterized by a compliance $C_F$ arranged to be adjacent to the ear canal characterized by a compliance $C_E$ when said shell is seated inside the concha, the volume of said front cavity being sufficiently large so that the front cavity compliance $C_F$ is greater than the ear canal compliance $C_E$ to furnish significant passive attenuation, and electronic circuitry intercoupling said first and second electroacoustical transducers and coacting therewith to provide active noise reduction by reproducing with said first electroacoustical transducer characterized by a compliance $C_D$ noise incident upon said second electroacoustical transducer but of opposite phase so as to actively reduce the noise intensity inside said concha, said compliance $C_D$ being greater than said compliance $C_F$.

2. Earphone apparatus in accordance with claim 1 wherein said front cavity is arranged to be closer to the inner ear than said rear cavity with said earphone apparatus inside the concha of an ear.

3. Earphone apparatus in accordance with claim 1 wherein said shell includes a snap-on ear cavity mold.

4. Earphone apparatus in accordance with claim 1 wherein said shell is formed with front and rear cavities arranged to be respectively nearer and further from the inner ear when seated inside the concha, said first electroacoustic transducer is a microphone in said front cavity, and said second electroacoustic transducer is a driver forming at least a portion of the boundary between said front and rear cavities.

5. Earphone apparatus in accordance with claim 4 wherein said front cavity is formed with an opening covered by material having acoustic resistance.

6. Earphone apparatus in accordance with claim 4 wherein the volume of said front cavity is less than about 10 cc.

7. Earphone apparatus in accordance with claim 3 wherein said front cavity is formed with an opening covered by material having acoustic resistance.

8. Earphone apparatus in an active noise reduction system comprising:

an assembly including a shell accommodating first and second closely adjacent electroacoustical transducers of shape and size that allows said shell and first and second electroacoustical transducers to fit inside the concha of the ear, and electronic circuitry intercoupling said first and second electroacoustical transducers and coacting therewith to provide active noise reduction by reproducing with said driver noise incident upon said microphone but of opposite phase so as to actively reduce the noise intensity inside said concha, wherein said shell is formed with front and rear cavities arranged to be respectively nearer and further from the inner ear when seated in said concha, wherein said front cavity is formed with an opening covered by material having acoustic resistance.

9. Earphone apparatus in an active noise reduction system comprising:

an assembly including a shell accommodating first and second closely adjacent electroacoustical transducers of shape and size that allows said shell and first and second electroacoustical transducers to fit inside the concha of the ear, and electronic circuitry intercoupling said first and second electroacoustical transducers and coacting therewith to provide active noise reduction by reproducing with said driver noise incident upon said microphone but of opposite phase so as to actively reduce the noise intensity inside said concha, wherein said shell is formed with front and rear cavities arranged to be respectively nearer and further from the inner ear when seated in said concha, said first electroacoustic transducer is a microphone in said front cavity, and said second electroacoustic transducer is a driver forming at least a portion of the boundary between said front and rear cavities.

wherein said front cavity at least partially coaxially surrounds said rear cavity.

10. Earphone apparatus in accordance with claim 9 wherein said front cavity is formed with an opening covered by material having acoustic resistance.

11. Earphone apparatus in an active noise reduction system comprising: Earphone apparatus in an active noise reduction system comprising:

an assembly including a shell accommodating first and second closely adjacent electroacoustical transducers of shape and size that allows said shell and first and second electroacoustical transducers to fit inside the concha of the ear, and electronic circuitry intercoupling said first and second electroacoustical transducers and coacting therewith to provide active noise reduction by reproducing with said driver noise incident upon said microphone but of opposite phase so as to actively reduce the noise intensity inside said concha, wherein said shell is formed with front and rear cavities arranged to be respectively nearer and further from the inner ear when seated in said concha, said first electroacoustic transducer is a microphone in said front cavity, and said second electroacoustic transducer is a driver forming at least a portion of the boundary between said front and rear cavities, wherein said front and rear cavities are largely filled with open cell foam.

12. Earphone apparatus in an active noise reduction system comprising:

an assembly including a shell accommodating first and second closely adjacent electroacoustical transducers of shape and size that allows said shell and first and second electroacoustical transducers to fit inside the concha of the ear, and electronic circuitry intercoupling said first and second electroacoustical transducers and coacting therewith to provide active noise reduction by reproducing with said driver noise incident upon said microphone but of opposite phase so as to actively reduce the noise intensity inside said concha, wherein said shell is formed with front and rear cavities arranged to be respectively nearer and further from the inner ear when seated in said concha, said first electroacoustic transducer is a microphone in said front cavity, and said second electroacoustic transducer is a driver forming at least a portion of the boundary between said front and rear cavities, wherein said microphone has a microphone diaphragm and said driver has a driver diaphragm perpendicular to said microphone diaphragm.

13. Earphone apparatus in accordance with claim 12 wherein said driver is heavily damped.

14. Earphone apparatus in an active noise reduction system comprising:

an assembly including a shell accommodating first and second closely adjacent electroacoustical transducers of shape and size that allows said shell and first and second electroacoustical transducers to fit inside the concha of the ear, and electronic circuitry intercoupling said first and second electroacoustical transducers and coacting therewith to provide active noise reduction by reproducing with said driver noise incident upon said microphone but of opposite phase so as to actively reduce the noise intensity inside said concha, further comprising a layer of silicon gel having a portion of the outside of said shell, and a layer of polyurethane film enclosing said silicon gel.

15. Earphone apparatus in a noise reduction system comprising:

an assembly including a shell of shape and size that allows said shell to fit inside the concha of the ear, wherein said shell is formed with at least a front cavity characterized by a compliance $C_F$ arranged to be adjacent to the ear canal characterized by a compliance $C_E$ when said shell is seated inside the concha, the volume of said front cavity being sufficiently large so that the front cavity compliance $C_F$ is greater than the ear canal compliance $C_E$ to furnish significant passive attenuation.

16. Earphone apparatus in accordance with claim 15 wherein said front cavity is formed with an opening covered by material having acoustic resistance.

17. Earphone apparatus in accordance with claim 15 wherein said front cavity is substantially the entire available volume of said shell.

18. Earphone apparatus in accordance with claim 17 wherein the volume of said front cavity is less than about 10 cc.

19. Earphone apparatus in accordance with claim 17 wherein said front cavity is formed with an opening covered by material having acoustic resistance.

20. Earphone apparatus in accordance with claim 15 wherein said shell is custom molded to the concha of the wearer.

21. Earphone apparatus in accordance with claim 20 wherein said shell includes a snap-on ear cavity mold.

22. Earphone apparatus in accordance with claim 15 wherein the volume of said front cavity is less than about 10 cc.

* * * * *

UNITED STATES PATENT AND TRADEMARK OFFICE
CERTIFICATE OF CORRECTION

PATENT NO.  : 5,305,387
DATED       : April 19, 1994
INVENTOR(S) : Roman Sapiejewski It is certified that error appears in the above-identified patent and that said Letters Patent is hereby corrected as shown below:

Title page, item [54] and col. 1, line 1,
In the title, "EARPONING" should read --EARPHONING--.

Column 1, line 1, "EARPONING" should read --EARPHONING--.

Line 15, after "driver" "," should be deleted.

Line 67, --1-- should be after "FIG.".

Column 2, line 18, "View" should be --view--.

Column 4, line 36, "section" should be --sections--.

Column 6, line 5, the "." should be --,--.

Lines 12-13, delete "Earphone apparatus in an active noise reduction system comprising:".

Column 7, line 10, "having" should be --along--.

Signed and Sealed this

Second Day of January, 1996

Attest:

BRUCE LEHMAN

Attesting Officer      Commissioner of Patents and Trademarks